(12) United States Patent
Koch et al.

(10) Patent No.: US 10,682,058 B2
(45) Date of Patent: Jun. 16, 2020

(54) DEVICE AND SYSTEM FOR DOPPLER OPTICAL COHERENCE TOMOGRAPHY (OCT) OF THE HUMAN MIDDLE EAR

(71) Applicant: Technische Universität Dresden, Dresden (DE)

(72) Inventors: Edmund Koch, Dresden (DE); Pascal Rottmann, Dresden (DE); Lars Kirsten, Freital (DE); Anke Burkhardt, Dresden (DE); Mirko Mehner, Hainichen (DE)

(73) Assignee: Technische Universität Dresden, Dresden (DE)

( * ) Notice: Subject to any disclaimer, the term of this patent is extended or adjusted under 35 U.S.C. 154(b) by 515 days.

(21) Appl. No.: 15/448,825

(22) Filed: Mar. 3, 2017

(65) Prior Publication Data
US 2017/0251924 A1 Sep. 7, 2017

(30) Foreign Application Priority Data

Mar. 4, 2016 (DE) .................. 10 2016 203 608

(51) Int. Cl.
*A61B 5/00* (2006.01)
*A61B 1/05* (2006.01)
(Continued)

(52) U.S. Cl.
CPC ........ *A61B 5/0066* (2013.01); *A61B 1/00163* (2013.01); *A61B 1/051* (2013.01);
(Continued)

(58) Field of Classification Search
CPC ... A61B 5/0066; A61B 5/0059; A61B 5/0084; A61B 5/0075; A61B 3/102; A61B 5/0077; A61B 2562/0204; A61B 2562/0247; A61B 5/0086; A61B 5/0073; A61B 8/12; A61B 5/6852; A61B 3/0091; A61B 18/20; A61B 5/7257; A61B 5/7275; A61B 2562/228;
(Continued)

(56) References Cited

U.S. PATENT DOCUMENTS

| 4,251,686 A * | 2/1981 | Sokolich | A61B 5/12 381/338 |
| 5,738,633 A * | 4/1998 | Christiansen | A61B 5/121 600/559 |

(Continued)

FOREIGN PATENT DOCUMENTS

| EP | 1215990 B1 | 10/2004 |
| EP | 2514356 A1 | 10/2012 |
| WO | 0064328 A1 | 11/2000 |

OTHER PUBLICATIONS

Fidanboylu et al., Fiber Optic Sensors and their Applications, (May 2009) (Year: 2009).*

(Continued)

*Primary Examiner* — Boniface N Nganga
(74) *Attorney, Agent, or Firm* — The Dobrusin Law Firm, P.C.

(57) ABSTRACT

A device for Doppler optical coherence tomography (Doppler OCT), preferably of the human middle ear, is proposed. The device has an endoscope unit for at least partial insertion into the auditory canal. A sound source, a sound receiver, and OCT optics are integrated in the endoscope unit.

20 Claims, 1 Drawing Sheet

(51) Int. Cl.
   *G01B 9/02* (2006.01)
   *A61B 1/00* (2006.01)
   *A61B 5/12* (2006.01)
   *A61B 1/227* (2006.01)

(52) U.S. Cl.
   CPC .............. *A61B 1/227* (2013.01); *A61B 5/125* (2013.01); *A61B 5/742* (2013.01); *G01B 9/02031* (2013.01); *G01B 9/02045* (2013.01); *G01B 9/02091* (2013.01); *A61B 1/00165* (2013.01)

(58) Field of Classification Search
   CPC ..... A61B 5/1459; A61B 6/4021; A61B 90/06; A61B 1/227; A61B 5/7278; A61B 2562/0233; A61B 5/0082; A61B 6/4405; A61B 2562/0242; A61B 5/6817; A61B 8/00; A61B 2560/0233; A61B 5/0062; A61B 5/1075; A61B 8/445; A61B 3/1225; A61B 5/72; A61B 2090/064; A61B 2090/306; A61B 5/12; A61B 5/7282; A61B 1/0646; A61B 2562/146; A61B 2576/02; A61B 3/103; A61B 5/6816; A61B 1/00009; A61B 5/7235; A61B 7/00; A61B 2017/00061; A61B 2090/3735; A61B 2560/0443; A61B 2562/0238; A61B 5/0053; A61B 8/4461; A61B 18/203; A61B 1/00172; A61B 5/0097; A61B 8/488; A61B 1/00096; A61B 1/00165; A61B 1/06; A61B 1/07; A61B 5/6815; A61B 5/6844; A61B 18/201; A61B 1/002; A61B 5/0051; A61B 1/0684; A61B 2018/2272; A61B 5/0093; A61B 8/0858; A61B 2018/00732; A61B 2018/202; A61B 5/066; A61B 5/051; A61B 5/125; A61B 5/742; A61B 1/00163; G01B 9/02091; G01B 9/02045; G01B 9/02031
   See application file for complete search history.

(56) References Cited

U.S. PATENT DOCUMENTS

| | | | |
|---|---|---|---|
| 7,236,243 B2 * | 6/2007 | Beecroft | G01J 3/02 356/328 |
| 8,594,757 B2 | 11/2013 | Boppart et al. | |
| 9,398,840 B2 | 7/2016 | Rehe | |
| 9,867,528 B1 * | 1/2018 | Boppart | A61B 1/2275 |
| 2005/0015018 A1 * | 1/2005 | Dolphin | A61B 1/227 600/559 |
| 2005/0143664 A1 * | 6/2005 | Chen | A61B 5/0066 600/478 |
| 2008/0026231 A1 | 1/2008 | Radtke et al. | |
| 2008/0262314 A1 | 10/2008 | Tearney et al. | |
| 2009/0018519 A1 | 1/2009 | Yoshida | |
| 2009/0185191 A1 | 7/2009 | Boppart et al. | |
| 2010/0094137 A1 * | 4/2010 | Furlong | A61B 1/042 600/477 |
| 2010/0217102 A1 * | 8/2010 | LeBoeuf | A61B 5/4812 600/310 |
| 2011/0130652 A1 | 6/2011 | Boppart et al. | |
| 2011/0137118 A1 * | 6/2011 | Huang | A61B 1/227 600/109 |
| 2012/0088976 A1 * | 4/2012 | Shehadeh | A61B 1/00101 600/187 |
| 2013/0006013 A1 | 1/2013 | Mattke et al. | |
| 2013/0060131 A1 | 3/2013 | Oghalai et al. | |
| 2013/0218022 A1 * | 8/2013 | Larsen | A61B 5/01 600/474 |
| 2013/0345556 A1 | 12/2013 | Courtney et al. | |
| 2015/0148654 A1 * | 5/2015 | Whanwook | A61B 3/102 600/407 |
| 2017/0049310 A1 * | 2/2017 | Lepple-Wienhues | A61B 1/00009 |

OTHER PUBLICATIONS

European Search Report for European Application No. 17159126; dated Jul. 20, 2017.
Anke Burkhardt et al: "Investigation of the human tympanic membrane oscillation ex vivo by Doppler optical coherence tomography" Journal of Biophotonics (2014).
Kirsten Lars et al: "Imaging the tympanic membrane oscillation ex vivo with Doppler optical coherence tomography during simulated Eustachian catarrh", OSA Publishing (Jul. 9, 2015).
Burkhardt Anke et al: Endoscopic optical coherence tomography for imaging the tympanic membrane II; OSA Publishing (Jun. 9, 2011).
European Search Report for German Patent Application No. 10 2016 203 608.4; dated Sep. 21, 2016.
Jesung Park, Investigation of middle ear anatomy and function with combined video otoscopy-phase sensitive OCT, Published Jan. 5, 2016.

\* cited by examiner

DEVICE AND SYSTEM FOR DOPPLER OPTICAL COHERENCE TOMOGRAPHY (OCT) OF THE HUMAN MIDDLE EAR

FIELD

The present invention is directed to a device for medical examination of the human eardrum.

RELATED APPLICATIONS

This application claims the benefit of DE 10 2016 203 608.4 filed on Mar. 4, 2016, the entirety of which is hereby incorporated by reference herein for all purposes.

BACKGROUND

The prior art has disclosed otoscopy, tympanometry, audiometry, laser Doppler vibrometry (LDV) and radiological imaging as methods for non-surgical examination of impaired hearing in a patient. Otoscopy involves an evaluation of the eardrum by a treating physician. However, it has the disadvantage that, on the one hand, it permits only a view of the eardrum and, on the other hand, it entails a purely subjective assessment by the physician. By contrast, in tympanometry, audiometry and other acoustic methods, the hearing ability or the impedance/compliance is measured, but only integral statements concerning the whole of the middle ear are possible. By contrast, an isolated assessment of the eardrum alone is not possible or is possible only with difficulty. Laser Doppler vibrometry is based on the frequency-resolved measurement of the vibration of the eardrum, but only at a single point of the eardrum. Corresponding devices for carrying out the aforementioned methods are disclosed, for example, in the documents WO 00/64 328 A1 and US 2008/0 262 314 A1.

To improve the early and reliable diagnosis of various pathologies, such as otitis media and tympanic effusion, and the locating of sound conduction disturbances, a spatially resolved and three-dimensional measurement of the structure of the human eardrum is desirable. A method by which this aim can be achieved is optical coherence tomography (OCT). This is a method which is known from the prior art and which permits contact-free, three-dimensional measurement of the structure of the human eardrum, in which method light from a broad-band, short-coherence light source is divided by a beam splitter into a sample beam and a reference beam, and the sample beam scattered on the eardrum to be examined is then superposed with the reference beam reflected on a mirror. The interfering beams are detected by spectral resolution. For example, in Fourier domain OCT, a depth profile of the reflectivity is calculated from an interference spectrum via Fourier transformation. To generate a three-dimensional image of the eardrum, the eardrum is scanned point by point in two lateral directions. An endoscope for carrying out the optical coherence tomography is known, for example, from the documents US 2013/0 060 131 A1, US 2009/0 185 191 A1 and U.S. Pat. No. 8,594,757 B2. With the extension to Doppler OCT, frequency-resolved measurements of the eardrum vibrations can be carried out in the context of an in vivo examination. As an alternative to frequency domain OCT, it is also possible to use time domain OCT or parallel or full-field OCT and further methods.

SUMMARY

It is an object of the present invention to make available a device which permits both a three-dimensional, spatially resolved measurement of the structure of the human eardrum and also a spatially resolved and frequency-resolved measurement of eardrum vibrations in the context of a non-invasive in vivo endoscopic examination and which at the same time also allows acoustic excitation of the eardrum vibration and measurement of the acoustic pressure in immediate proximity to the eardrum. The device is also intended to have a simple design and be cost-effective to produce and comply with current legal requirements placed on a medical product.

This object is achieved with a device for Doppler optical coherence tomography (Doppler OCT) of the human middle ear, wherein the device has an endoscope unit for at least partial insertion into the auditory canal, a sound receiver, and OCT optics.

Compared to the prior art, the device according to the invention has the advantage that the endoscope unit comprises both the sound source for well-conditioned, direct acoustic stimulation of the eardrum and also the sound-measuring unit for measuring the acoustic pressure in the area in front of the eardrum, and also the OCT optics, such that Doppler optical coherence tomography can be performed during the defined stimulation of the eardrum by the sound source. The Doppler optical coherence tomography permits a measurement of the vibration of the eardrum by using the measured Doppler shift to infer the movement of the eardrum. In particular, the sound receiver permits referencing of the eardrum reactions to the acoustic signal as measured by means of the optical coherence tomography. By the simultaneous measurement of the acoustic pressure in front of the eardrum, the measured Doppler shift can moreover be converted to a phase relationship for the acoustic stimulation. Therefore, this permits not only a three-dimensional spatially resolved measurement of the structure of the human eardrum by means of the optical coherence tomography, but at the same time also a spatially resolved and frequency-resolved measurement of the eardrum vibrations by means of Doppler OCT. Moreover, the use of sound source and sound receiver permits a comparison between emitted and reflected acoustic power. The reliable and early diagnosis of pathologies such as otitis media, tympanic effusion and sound conduction disturbances, and the examination of patients already with middle ear reconstruction, can thus be greatly improved. The treating physician advantageously requires only the one device according to the invention, such that practical handling for the treating physician remains largely the same as with conventional endoscopes. Advantageously, the acoustic stimulation and the sound measurement with the device according to the invention take place directly in front of the eardrum. The auditory canal is thus excluded as acoustic modulator from the measurement chain. The advantage of this arrangement lies in a clearly defined, direct coupling of sound source and sound receiver (eardrum). The sound source is typically also designated as a sound transmitter or, in such a use, also as a loudspeaker.

The device according to the invention is in particular an endoscope add-on, which is adapted to given OCT measurement heads. Such an OCT measurement head is typically connected as part of an OCT system to an OCT central unit. The OCT system comprises a beam source and a beam splitter, by means of which broad-band, short-coherence light from the beam source is divided into a sample beam and a reference beam. The beam splitter is either integrated in the OCT measurement head or arranged in the OCT central unit. The OCT measurement head comprises at least one possibility of beam deviation, e.g. by means of galvanometer scanners. The sample beam is coupled from the OCT measurement head into the OCT optics of the endoscope unit and thus diverted to the eardrum. The sample beam reflected on the eardrum is conveyed back through the OCT optics into the OCT measurement head and is superposed, in the OCT measurement head or in the OCT central unit, with the reference beam reflected on a mirror. The interfering beams are evaluated by means of an evaluation unit. To generate a three-dimensional image of the eardrum, the eardrum is in this case scanned point by point. An interferometer can be implemented in various ways. Either the interferometer, i.e. reference arm and sample arm, is integrated in the OCT measurement head or the beam splitter of the interferometer (e.g. a fused fibre coupler) is located in the OCT central unit. The sample arm is then composed of a glass fibre that leads to the OCT measurement head. For the measurement head, this means that the latter does not necessarily have to contain the entire interferometer. Only a unit for the beam deviation is integrated in any case. Alternatively, however, so-called common-path OCT would also be conceivable, which does without a traditional interferometer and instead comprises an additional optical element at whose interface light from the beam is reflected which directly interferes with the sample beam reflected on the eardrum. The reference arm and the sample arm thus come together at least partially. It is conceivable that the optical element, for example a glass plate, is integrated in the OCT optics or is provided at the eardrum-side output of the OCT optics. In Doppler OCT, the Doppler shift in the reflected sample beam, effected by the scattering of the sample beam on the vibrating or moved eardrum, is additionally taken into account. The data processing can take place in a known manner in the context of time domain OCT (TD-OCT) or Fourier domain OCT (FD-OCT), in particular swept source OCT (SS-OCT), and with extensions of the data evaluation, e.g. phase-resolved Doppler OCT and/or polarization-sensitive OCT (PS-OCT) and/or spectroscopic OCT (SD-OCT). The beam source in particular emits light in the IR range. Alternatively, however, it would also be conceivable that the beam source at least partially emits light in the visible range.

Advantageous embodiments and developments of the invention can be found in the dependent claims, and in the description with reference to the drawings.

According to a preferred embodiment of the present invention, provision is made that the device comprises a main body and preferably an exchangeable attachment, wherein the attachment particularly preferably has a base area, which can be secured releasably on the main body, and a mouth area which is directed towards the eardrum during use of the device. Advantageously, the device is thus in two parts, namely main body and attachment. Only the attachment comes into direct contact with the patient, such that only the attachment part has to be exchanged or cleaned and sterilized from patient to patient in order to maintain the required hygiene. It is conceivable that the attachment is made of a sterilizable material such as metal. The attachment is shaped as a funnel which is provided for holding and stabilizing the OCT optics, acoustic leads and, if appropriate, light guides. The main body preferably has all the active components, while the attachment preferably has exclusively passive components.

According to another preferred embodiment of the present invention, provision is made that the OCT optics are designed such that an OCT sample beam coupled in at the base area is conveyed to the mouth area, and the sample beam reflected on the eardrum is transported back to the base area. The sample beam is either coupled in from an external OCT measurement head or made available by an OCT measurement head integrated in the main body. The reflected or scattered sample beam is returned for evaluation to the OCT measurement head or to the OCT central unit. For this purpose, the OCT optics preferably comprise a lens system, particularly preferably one or more gradient index (GRIN) lenses or one or more rod lenses. The OCT optics preferably comprise a combination of GRIN relay lenses and GRIN objective lenses. This has the advantage that the sample beam is widened, thereby achieving a wide viewing field in the comparatively narrow auditory canal. This is a particular advantage over the methods known from the prior art since, on account of the variable geometries of the auditory canal, the customary telecentric scanning methods do not permit a complete view of the eardrum.

If an external OCT measurement head is used, the main body has in particular a coupling area for coupling the device to the external OCT measurement head, wherein the coupling area is designed in such a way that, in the coupled state, the OCT sample beam from an OCT scanner of the OCT measurement head is coupled into the OCT optics and the reflected OCT sample beam is transported back to the OCT scanner. For this purpose, the OCT measurement head has a beam deflection unit.

The OCT optics are preferably part of the attachment. Alternatively, however, it would also be conceivable that the OCT optics are part of the main body. The OCT optics are preferably likewise used for otoscopy and in particular for optical video endoscopy, which is carried out simultaneously to the (Doppler) OCT measurement. It is conceivable that the reflected sample beam in the OCT measurement head is diverted onto a semi-transmitting/dichroic mirror, which deflects light of the visible spectrum onto an optical camera, for example a CCD chip or onto an eyepiece. Alternatively, however, it would also be conceivable that the endoscope unit and in particular the attachment has, in addition to the OCT optics, a separate optical image transmission unit which serves to transmit image information for otoscopy or optical video endoscopy.

According to another preferred embodiment of the present invention, provision is made that the attachment is provided with an ear mould for sealing the auditory canal. The ear mould comprises in particular a disposable article which is pushed over the attachment. The ear mould preferably has an outer contour which is at least partially adapted to the inner contour of the human auditory canal, such that the insertion of the device into the auditory canal of a patient is as simple as possible and is comfortable for patient. The ear mould in this case serves to seal the auditory canal such that a defined pressure, which may deviate from the ambient pressure, is adjustable in the auditory canal for tympanometry.

According to another preferred embodiment of the present invention, provision is made that the endoscope unit has a light unit, wherein the light unit comprises a light source, a connector for connection of an external light source and/or a light guide. The light unit moreover preferably comprises a light source which is arranged within the main body, wherein the light guide carries the light of the light source to the middle ear such that the eardrum is illuminated for otoscopy. Alternatively, however, it would also be conceivable that the light unit comprises a light source which is arranged directly in the mouth area. In this case, only the electrical power supply in the form of an electrical lead would run through the attachment. For example, the light source could be a compact light-emitting diode (LED). Moreover, it would also be conceivable that the light unit comprises a connector for connection to an external light source or a further light guider, wherein the connector is preferably integrated in the main body. The external light source could be integrated in the OCT measurement head, such that the device according to the invention itself has no light source, and instead only the light emerging from the measurement head leads to the eardrum. The light guide comprises in particular a glass fibre or a glass fibre bundle and is at least partially integrated in the attachment. The light source emits in particular light in the visible spectrum. Alternatively, illumination could also take place via the OCT optics.

According to another preferred embodiment of the present invention, provision is made that the attachment comprises an acoustic outgoing conductor for conveying sound from the sound source to the mouth area, wherein the outgoing conductor preferably comprises a small tube and particularly preferably a small metal tube. Analogously, the attachment preferably comprises an acoustic return conductor for conveying sound from the mouth area to the sound receiver, wherein the return conductor preferably comprises a small tube and particularly preferably a small metal tube. The outgoing conductor and/or the return conductor are either arranged inside or outside of the attachment. The sound source is preferably arranged in the main body. Alternatively, however, it would also be conceivable that the sound source is arranged directly in the mouth area of the attachment. The acoustic sound receiver preferably comprises a microphone, wherein the acoustic sound receiver is preferably integrated in the main body, wherein the sound is conveyed from the mouth area through the return conductor to the microphone. The sound source and the sound receiver are acoustically uncoupled from each other in the main body. It is conceivable that the sound source and the sound receiver are for this purpose each mounted in a silicone pouch, these each being connected to the main body only via a narrow silicone holder. Alternatively, it would also be conceivable that the microphone is arranged directly in the mouth area. In this case, the recorded acoustic signals are conveyed via electrical signal lines to the main body and in particular to the OCT measurement head.

According to another preferred embodiment of the present invention, provision is made that the device has an adjusting device which is provided for adjusting a distance between the coupling area and the optical image transmission unit, wherein the adjusting device preferably comprises an adjusting gear for the longitudinal displacement of the optical image transmission unit relative to the main body. The adjusting device advantageously make sit possible to adjust a working distance and the size of the viewing field. For this purpose, the distance between the OCT optics and the external OCT measurement head coupled to the endoscope unit is in particular adjusted by means of the adjusting device. It is conceivable that, with the aid of the adjusting device, the OCT optics are movable relative to the coupling area. For this purpose, the main body comprises a stationary base part, which comprises the coupling area and an adjustment part which is movable relative to the base part by means of the adjusting device and on which the seat for the attachment and thus also the OCT optics are secured. The adjustment part in this case preferably also comprises the sound source, the sound receiver and part of the light unit. The adjusting device has an adjusting gear which converts a relative rotation movement between the base part and a part of the adjusting device into a translation movement of the adjustment part relative to the base part, as a result of which in particular the distance between the scanner-side end of the gradient index lens or the rod lens and the external OCT scanner changes. Alternatively, it would also be conceivable that the adjusting device is configured in the form of a varifocal lens which in particular is arranged between the OCT optics and the OCT measurement head or is part of the OCT optics. The varifocal lens could also replace the objective lens (triplet) in the OCT measurement head.

Since the eardrum is not perpendicular to the auditory canal, another embodiment has a mirror or a prism at the eardrum-side end of the endoscope. Rigid or adjustable deflection units of this kind are known, for example, from the documents EP 2514356 A1 and EP 1215990 B1 or from the product information on borescopes from Karl Storz.

According to another preferred embodiment of the present invention, provision is made that the main body comprises an internal OCT scanner which couples the sample beam into the OCT optics and is provided for scanning the eardrum, and possible also an evaluation unit for performing Doppler optical coherence tomography (Doppler OCT) on the basis of image information and sound information provided by the OCT scanner and by the microphone. Thus, the whole Doppler OCT data evaluation is advantageously carried out inside the endoscope unit.

According to another preferred embodiment of the present invention, provision is made that the endoscope unit has an additional pressure channel via which the pressure in the area of the auditory canal can be influenced. The pressure channel is connected to a pressure source, wherein the pressure source is preferably integrated in the main body or in the OCT measurement head. Alternatively, the pressure channel can completely or partially coincide with one of the acoustic leads, the outgoing conductor or return conductor. The pressure channel can extend internally or externally. The pressure source can be provided to give an underpressure and/or overpressure. In order to set a defined pressure in the auditory canal, the auditory canal has to be closed off in a pressure-tight manner relative to the ambient pressure. For this purpose, the endoscope unit is preferably provided with a corresponding ear mould or with a silicone dome pushed over the endoscope tube.

The present invention further relates to a system for optical coherence tomography, preferably Doppler optical coherence tomography (Doppler OCT), of the human eardrum, said system having an OCT measurement head and a device according to the invention coupled to the OCT measurement head. The OCT measurement head preferably has the OCT scanner and is preferably connected to an OCT central unit in which the evaluation unit is integrated for carrying out Doppler optical coherence tomography on the basis of image and sound information supplied by the OCT measurement head and by the microphone.

Further details, features and advantages of the invention will become clear from the drawings and also from the following description of preferred embodiments with reference to said drawings. The drawings merely depict illustrative embodiments of the invention, which do not limit the basic concept of the invention.

EMBODIMENTS OF THE INVENTION

In the various figures, identical parts are always provided with the same reference signs and are therefore generally also named or mentioned just once in each case.

Figure 1:
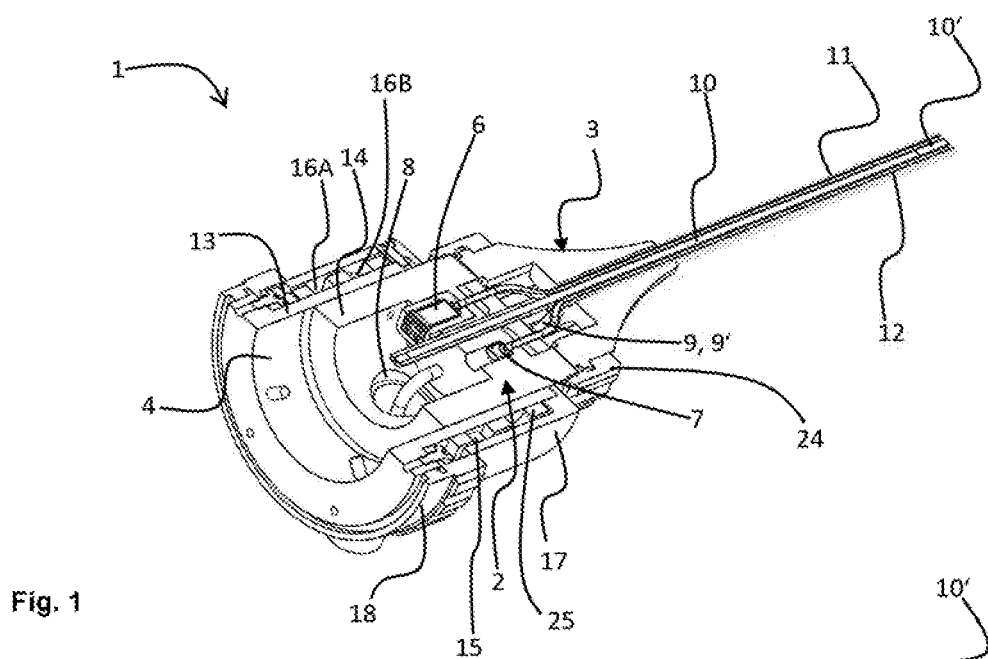
FIGS. 1 and 2 show schematic sectional views of a device for Doppler optical coherence tomography (Doppler OCT) of the human eardrum according to an illustrative embodiment of the present invention.
Figure 2:
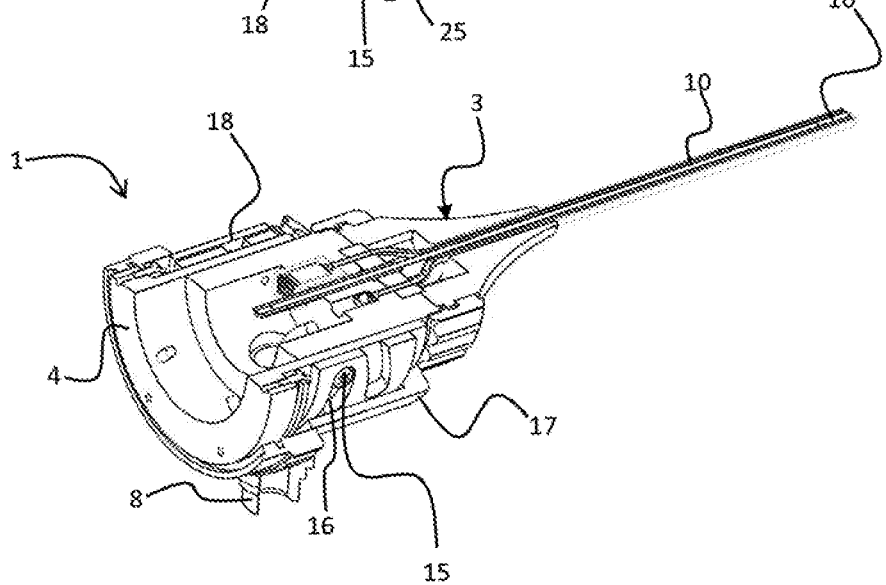

FIGS. 1 and 2 show schematic sectional views of a device 1 for Doppler optical coherence tomography (Doppler OCT) of the human eardrum according to an illustrative embodiment of the present invention.

In the present example, the device 1 comprises an endoscope unit (also designated as an endoscope add-on) which can be fitted onto an OCT measurement head 5 (cf. FIG. 3) of an OCT system 21. The endoscope unit comprises a main body 2, and an attachment 3 which is plugged releasably onto the main body 2 and is secured with a union nut 24. The main body 2 comprises a coupling area 4, with which the main body 2 is coupled to the OCT measurement head 5. Moreover, a sound source 6 and a sound receiver 7 in the form of a microphone are integrated in the main body 2. The main body 2 finally has a connector 8 for an external light source (not shown) via which light from the external light source is coupled in. The external light source in particular provides light in the visible spectrum.

The attachment 3 comprises a base area, which faces towards the OCT measurement head 5, and a mouth area, which faces towards the eardrum during use. The attachment 3 is inserted at least slightly into the auditory canal of a patient. From the base area to the mouth area, the attachment 3 has a strongly tapering design in order to improve the ergonomics. Arranged in the interior of the attachment 3 there are several sound and light guides which are supported and held by the wall of the attachment 3. In the present example, the wall of the attachment 3 is for this purpose made of metal, as a result of which the necessary hygiene requirements can at the same time be ensured. Moreover, the attachment 3 is exchangeable and sterilizable, such that either a new attachment or a freshly sterilized attachment 3 can be fitted onto the main body 2 from patient to patient. The attachment 3 comprises a light unit 9 functioning as a light guide 9' in the form of a glass fibre bundle, into which the light from the external light source is coupled and is conveyed to the mouth area. The light emerging from the light unit 9 in the mouth area serves to illuminate the eardrum. The reflected light serves for otoscopy by the treating physician or for optical video endoscopy by means of a camera, for example a CCD camera.

Moreover, the attachment 3 has OCT optics 10 which run parallel to the light guide 9' between the mouth area and the base area. The OCT optics 10 comprise one or more lenses or rod lenses 10' and preferably a gradient index lens or a combination of gradient index lenses and further optical elements. The end of the OCT optics 10 towards the base area end protrudes into the coupling area 4, such that a sample beam provided by the OCT measurement head 5 can be coupled into the OCT optics 10 and is conveyed by means of the OCT optics 10 from the base area to the mouth area, where the sample beam emerges from the OCT optics 10 and impinges on the eardrum. The sample beam scattered and reflected on the eardrum enters the OCT optics 10 in the mouth area and is conveyed back to the base area and thus to the OCT measurement head 5. There, the sample beam impinges on further components of the OCT system 21 in which the sample beam is brought into interference with a reference beam by means of an interferometer, in order to generate an image of the structure of the eardrum. To ensure that a spatially resolved, three-dimensional image of the structure of the eardrum can be generated by the OCT system 21, the sample beam is moved systematically across the eardrum, and the eardrum is scanned with spatial resolution with the aid of an OCT scanner 20.1 of the OCT system 21. A beam deviation for the systematic scanning of the eardrum could preferably take place in the OCT measurement head 5 or could alternatively be arranged in the main body 2 or in the mouth area.

A semi-transmitting mirror is provided within the OCT measurement head 5 or within the main body 2, which mirror filters light in the visible spectrum out of the reflected sample beam and leads it for otoscopy purposes onto an eyepiece or for purposes of optical video endoscopy onto a CCD camera. In this way, traditional optical otoscopy/endoscopy can be performed parallel to the OCT. The semi-transmitting mirror and the CCD camera are optionally integrated in the main body 2 of the endoscope unit. Alternatively, it would also be conceivable that, for otoscopy, an additional image transmission unit is provided in the attachment or a CCD camera is provided in the mouth area.

The attachment 3 moreover has an acoustic outgoing conductor 11 in the form of a small metal tube. Acoustic waves, which are emitted by the sound source 6, are conveyed through the acoustic outgoing conductor 11 to the mouth area in order to stimulate the eardrum in a defined manner. The vibrated eardrum can now be analyzed by means of the OCT scanner 20.1, and a frequency-resolved and spatially resolved measurement of the eardrum vibration can be performed by means of the Doppler OCT, additionally taking account of the Doppler shift in the sample beam, which is caused by the scattering of the sample beam on the vibrating or moved eardrum. The data processing can take place in a known manner in the context of time domain OCT (TD-OCT) or Fourier domain OCT (FD-OCT), in particular swept source OCT (SS-OCT). The endoscope unit thus permits Doppler OCT at the same time as the OCT and the otoscopy. Similarly, the data evaluation can conceivably be extended, e.g. in the sense of polarization-sensitive OCT or spectroscopic OCT (SD-OCT).

The OCT optics 10 function as optics for the OCT scanner 20.1. To set the optical parameters such as working distance and size of the viewing field, the endoscope unit has an adjusting device with which the distance between the OCT scanner 20.1 or the coupling area 4 and the end of the OCT optics 10 towards the base area end is adjustable. For this purpose, the main body 2 has a base part 13, and an adjustment part 14 movable with respect to the base part 13.

The base part 13 comprises the coupling area 4, while the adjustment part 14 is connected to the attachment 3. A relative movement between base part 13 and adjustment part 14 in the longitudinal direction thus has the effect that the distance between the OCT scanner 20.1 and the OCT optics 10 changes. The base part 13 and the adjustment part 14 are coupled to each other via an adjusting gear. The adjusting gear comprises an outer hollow cylinder 25 in which guide grooves 16 are introduced. The hollow cylinder 25 has guide grooves 16A which have no pitch in the longitudinal direction, i.e. extend strictly in the circumferential direction. At least two guide pins 15 protruding radially outward from the base part 13 run in these guide grooves 16A, which guide pins 15 fix base part 13 and hollow cylinder 25 relative to each other in the longitudinal direction and nevertheless permit a rotational movement between base part 13 and hollow cylinder 25. Moreover, the hollow cylinder 25 also has guide grooves 16B which extend like a thread obliquely across the circumference of the hollow cylinder 25, i.e. not only have a directional component in the circumferential direction but also directional component in the longitudinal direction. Two guide pins (not seen in the figures for reasons of perspective) protruding radially outward from the adjustment part 14 run in these oblique guide grooves 16B, as a result of which a rotation of the adjustment part 14 relative to the hollow cylinder 25 leads to a longitudinal movement between adjustment part 14 and hollow cylinder 25 and thus also to a longitudinal movement between adjustment part 14 and base part 13. In this way, therefore, the distance of the OCT optics 10 from the OCT measurement head 5 can be adjusted.

To ensure that the guide pins of the adjustment part 14 protrude into the guide grooves 16B, the base part 13, which is arranged radially between the adjustment part 14 and the hollow cylinder 25, has corresponding recesses designed as oblong holes for the guide pins of the adjustment part 14, which at the same time suppress a rotation of the adjustment part 14. To screen the adjusting gear, a housing 17 is provided in which the hollow cylinder 25 is encapsulated.

Moreover, an adjustment ring 18 is provided which is connected to the hollow cylinder 25 in such a way that only the adjustment ring 18 has to be manually rotated relative to the housing 17 by the user in order to permit adjustment. The connector 8 for the light guide 9' is arranged in the area of the adjustment part 14 through the housing 17, such that the light connection is not interrupted during the adjustment.

In the present example, the attachment 3 additionally has an acoustic return conductor 12, which is preferably likewise designed as a small metal tube and conveys sound waves in the area of the ear drum to the sound receiver 7. By means of the sound receiver 7, conventional tympanometry can also be performed in addition to the OCT and Doppler OCT, in conjunction with a system which generates an underpressure/overpressure and which uses an additional pressure channel to generate a static pressure change in the auditory canal. The pressure channel can alternatively coincide completely or partially with the outgoing conductor or return conductor and can run externally or internally. In order to set the defined pressure in the auditory canal, the auditory canal has to be sealed off in a pressure-tight manner relative to the environment. For this purpose, the endoscope unit is preferably provided with a corresponding ear mould. Moreover, in Doppler OCT, it is possible to determine the phase relationship between the stimulation of the ear drum and the movement or vibration of the ear drum measured by the Doppler shift.

Figure 3:
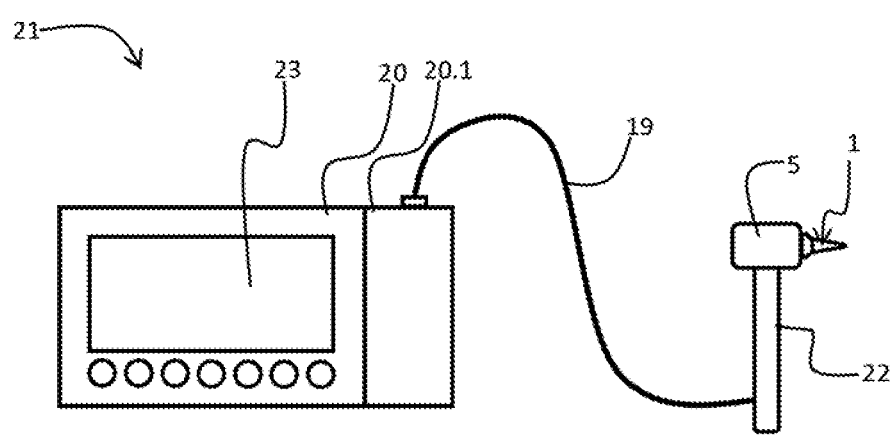
FIG. 3 shows a schematic view of a system for Doppler optical coherence tomography (Doppler OCT) of the human eardrum according to the illustrative embodiment of the present invention.

A system 21 for Doppler optical coherence tomography (Doppler OCT) of the human eardrum according to the illustrative embodiment of the present invention is shown in FIG. 3.

The OCT system 21 shown in FIG. 3 comprises the device 1 shown in FIGS. 1 and 2, and also an OCT measurement head 5. The OCT measurement head 5 is embedded here in a manual endoscope which is optionally provided with a handle 22 and is connected via a line 19 to an OCT central unit 20. The endoscope unit is connected to the OCT measurement head 5 via the above-described coupling area 4. An OCT scanner 20.1 integrated in the OCT measurement head 5 can thus perform the OCT and Doppler OCT. The OCT measurement head 5 moreover has the light source, which is coupled into the light guide 9' via the connector 8.

The recorded data of the OCT measurement head 5 are transferred digitally or optically to the central unit 20 and are evaluated there. It is conceivable that the central unit 20 has a corresponding evaluation unit for performing the Doppler optical coherence tomography on the basis of image and sound information supplied by the OCT scanner 20.1 and by the microphone. Moreover, the central unit 20 has a screen 23 on which the results of the OCT and Doppler OCT and optionally additional image information are displayed for video endoscopy/otoscopy and tympanometry. The endoscope unit or the central unit 20 are preferably equipped with signal elements, such as acoustic signal transmitters or lights, in order to indicate to the treating physician the end of the measurement procedure, for example, or a defined operating state. It is also conceivable that the measurement head or the endoscope, or the handle of the endoscope, is provided with buttons by which measurement procedures can be started, stopped and the like.

LIST OF REFERENCE SIGNS 1 device
2 main body
3 attachment
4 coupling area
5 OCT measurement head
6 sound source
7 sound receiver
8 connector for an external light source
9 light unit
9' light guide
10 OCT optics
10' lense or rod lense
11 outgoing conductor (acoustic)
12 return conductor (acoustic)
13 base part
14 adjustment part
15 guide pins
16 guide groove
17 housing
18 adjustment ring
19 line
20 central unit
20.1 OCT Scanner
21 OCT system
22 grip/handpiece
23 screen
24 union nut
25 hollow cylinder

The invention claimed is:

1. A device comprising:
an endoscope unit for at least partial insertion into an auditory canal, the endoscope unit comprising: a main body and an exchangeable attachment,
wherein a sound source, a sound receiver, and an (Optical Coherence Tomography) OCT optics are integrated in the endoscope unit,
wherein the exchangeable attachment comprises: a base area that is releasably secured on the main body, a mouth area that is configured to be directed towards an eardrum during use of the device, and an acoustic outgoing conductor for conveying sound from the sound source to the mouth area,
wherein the acoustic outgoing conductor comprises a metal tube, and
wherein the device is configured for Doppler optical coherence tomography of a middle ear of the human.

2. The device according to claim 1, wherein the OCT optics are designed such that an OCT sample beam coupled at the base area is conveyed to the mouth area, and the OCT sample beam reflected on the eardrum is transported back to the base area.

3. The device according to claim 1, wherein the OCT optics comprise an optical lens system comprising: one or more gradient index lenses or one or more rod lenses, and
wherein the OCT optics are part of the exchangeable attachment of the device.

4. The device according to claim 1, wherein the main body has a coupling area for coupling to an external OCT measurement head,
wherein in a coupled state, an OCT sample beam from an OCT scanner is coupled into the OCT optics and a reflected OCT sample beam is transported back to the OCT scanner.

5. The device according to claim 1, wherein the endoscope unit has a light unit, and
wherein the light unit comprises a connector for connection of an external light source and/or a light guide.

6. The device according to claim 5, wherein the light guide comprises a glass fibre or a glass fibre bundle and is integrated in the exchangeable attachment of the device and/or in the main body of the device, and/or wherein the connector is integrated in the main body.

7. The device according to claim 1, wherein the exchangeable attachment comprises an acoustic return conductor for conveying sound from the mouth area to the sound receiver, and
wherein the return conductor comprises a metal tube.

8. The device according to claim 1, wherein the sound receiver is integrated in the main body and comprises a microphone.

9. The device according to claim 1, wherein the sound source is integrated in the main body.

10. The device according to claim 1, wherein the exchangeable attachment is provided with an ear mould for sealing the auditory canal.

11. The device according to claim 1, wherein the main body of the device has an adjusting device, which is provided for adjusting a distance between a coupling area and an optical image transmission unit,
wherein the adjusting device comprises an adjusting gear for longitudinal adjustment of the optical image transmission unit relative to the coupling area.

12. The device according to claim 1, wherein the main body of the device comprises an internal OCT measurement head.

13. The device according to claim 12, wherein the device has an evaluation unit for performing the Doppler optical coherence tomography on a basis of image and sound information supplied by an OCT scanner and by a microphone.

14. The device according to claim 1, wherein the device comprises a nut that is configured to releasably secure the exchangeable attachment to the main body.

15. The device according to claim 1, wherein the OCT optics run parallel to a light guide, between the mouth area and the base area.

16. The device according to claim 1, wherein the metal tube extends along a center longitudinal axis of the attachment.

17. The device according to claim 1, wherein the device comprises a light guide that comprises a glass fibre or a glass fibre bundle that is integrated in the exchangeable attachment of the device.

18. The device according to claim 17, wherein the device comprises a nut that is configured to releasably secure the exchangeable attachment to the main body.

19. A system for Doppler optical coherence tomography of a human eardrum, the system having an OCT measurement head and a device coupled to the OCT measurement head, the device comprising:
an endoscope unit for at least partial insertion into an auditory canal of the human eardrum, the endoscope unit comprising a main body and an exchangeable attachment,
wherein a sound source, a sound receiver, and OCT optics are integrated in the endoscope unit,
wherein the exchangeable attachment comprises: a base area that is releasably secured on the main body, a mouth area that is configured to be directed towards an eardrum during use of the device, and an acoustic outgoing conductor for conveying sound from the sound source to the mouth area,
wherein the acoustic outgoing conductor comprises a metal tube, and
wherein the device is configured for Doppler optical coherence tomography of a middle ear of the human.

20. The device according to claim 16, wherein the metal tube extends through the main body and the attachment, the main body comprises the sound source and the sound receiver, the attachment is located distal of the main body.

* * * * *